United States Patent [19]
Shedlock

[11] Patent Number: 5,114,415
[45] Date of Patent: May 19, 1992

[54] APPARATUS FOR SUCTIONING SECRETIONS FROM UPPER AIRWAYS

[76] Inventor: Susan Shedlock, 3 Ironwood Ct., Stony Point, N.Y. 10980

[21] Appl. No.: 765,465

[22] Filed: Sep. 26, 1991

Related U.S. Application Data

[63] Continuation-in-part of Ser. No. 365,783, Jun. 14, 1989.

[51] Int. Cl.$^5$ .................... A61M 1/00; A61M 31/00; A61M 1/06; A61M 11/00
[52] U.S. Cl. .................... 604/319; 604/54; 604/73; 604/94
[58] Field of Search ............. 604/54, 73, 75, 76, 604/94, 118, 119, 220, 239, 310, 313, 318, 316, 319; 222/402.12, 402.2

[56] References Cited

U.S. PATENT DOCUMENTS

| | | | |
|---|---|---|---|
| 1,533,618 | 4/1925 | Taylor, Jr. | 604/94 |
| 2,052,321 | 8/1936 | Smart | 604/94 |
| 2,078,180 | 4/1937 | Kronenberg | 604/94 |
| 2,511,973 | 6/1950 | La Sierra, Jr. | 604/94 |
| 4,258,714 | 3/1981 | Leopoldi et al. | 604/212 |
| 4,403,611 | 9/1983 | Babbitt et al. | 604/118 |

FOREIGN PATENT DOCUMENTS

| | | | |
|---|---|---|---|
| 8905134 | 6/1989 | World Int. Prop. O. | 604/54 |
| 8905163 | 6/1989 | World Int. Prop. O. | 604/54 |

*Primary Examiner*—Randall L. Green
*Assistant Examiner*—R. Clarke
*Attorney, Agent, or Firm*—Ostrolenk, Faber, Gerb & Soffen

[57] ABSTRACT

Apparatus for removing fluid secretions from a patient's upper airway includes a power driven suction generator connected to one end of a flexible tube and a nozzle removably connected to the other end of the tube. The nozzle is constructed to be manually positioned and maintained in an operative position adjacent oropharynx and nasopharynx openings and is proportioned relative to such openings to permit not more than minimal insertion of the nozzle through such openings. In one embodiment the nozzle is constructed of rigid material and is adapted to be utilized as a nozzle for a manually operated nose syringe. In another embodiment the nozzle is constructed of relatively soft rubber-like material and is essentially of the same gradually tapered shape as the nozzle portion of a manually operated ear syringe.

7 Claims, 2 Drawing Sheets

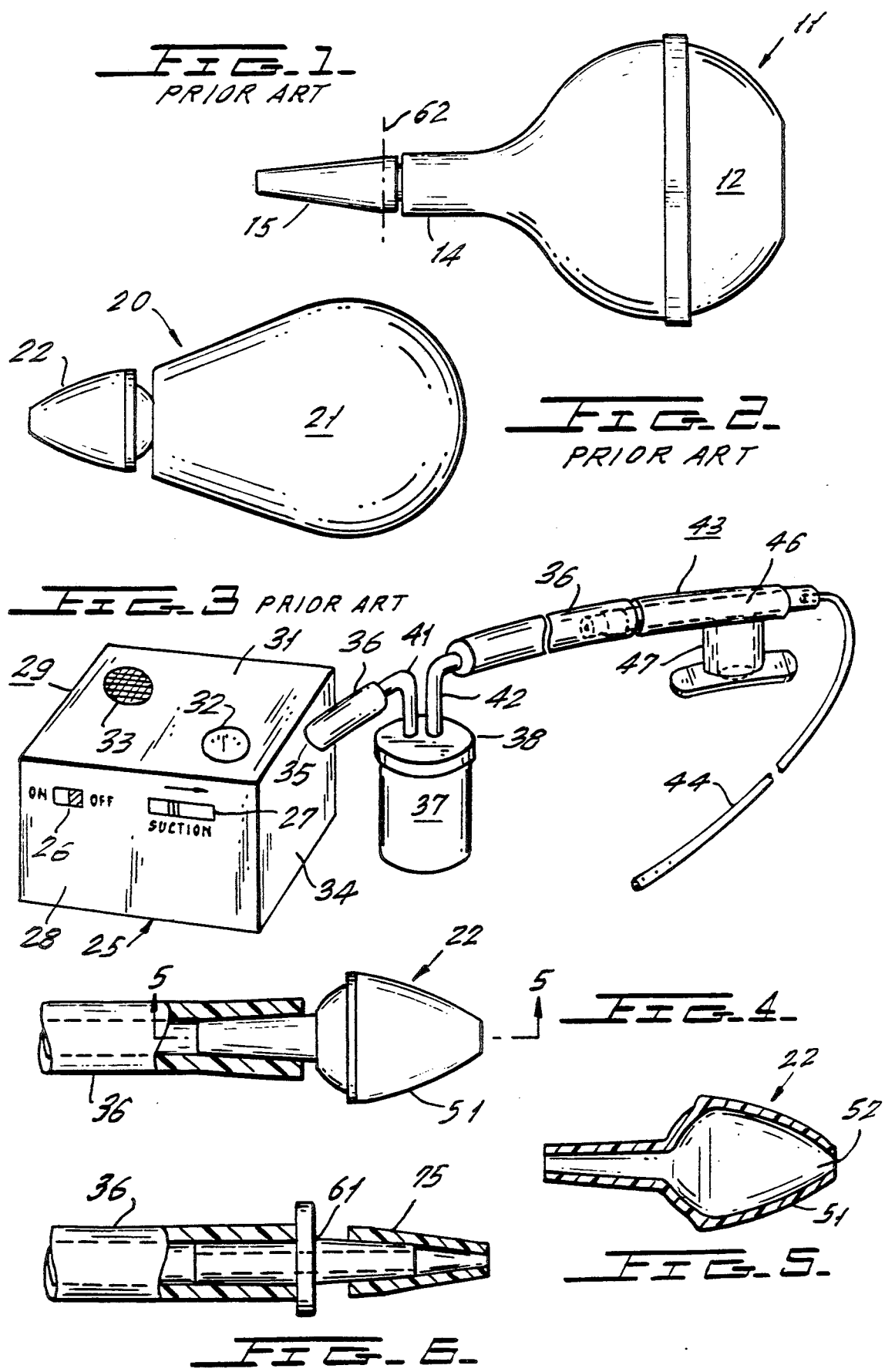

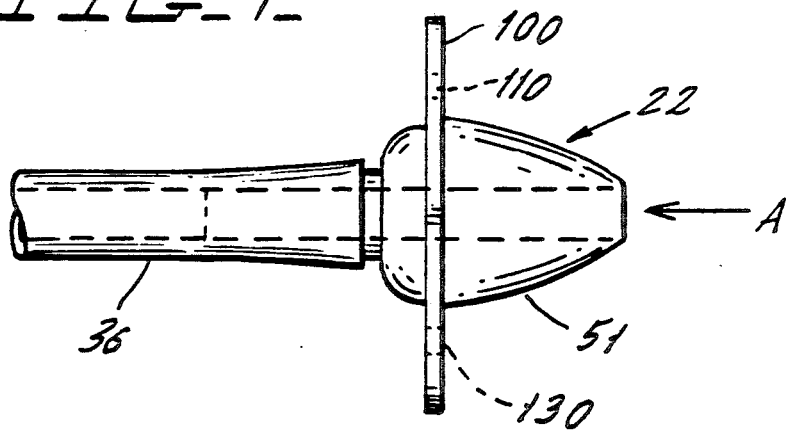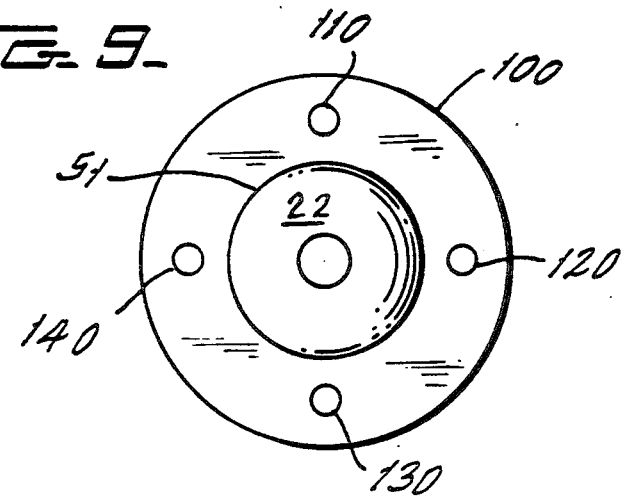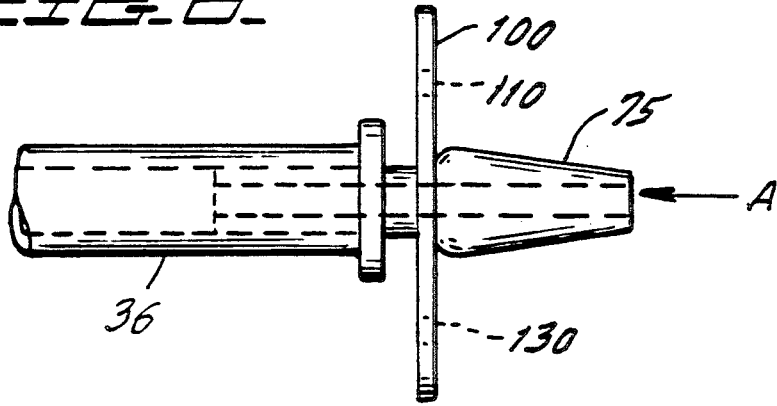

APPARATUS FOR SUCTIONING SECRETIONS FROM UPPER AIRWAYS

This is a continuation-in-part of application Ser. No. 365,783 filed on Jun. 14, 1989.

BACKGROUND OF THE INVENTION

This invention relates to suction adapter devices in general, and more particularly relates to devices of this type that are utilized to keep the oropharynx and nasopharynx free from secretions, to maintain a patent airway in sick infants, children and adults with respiratory compromise There are many conditions which require adults, children and very young infants that are seriously ill to be cared for at home for an extended period of time. While this care may be given by a nurse it is frequently given by a non-professional, typically the parent. When this type of extended and immediate care requires suctioning of fluid secretions through the infant's nose or mouth, a number of problems may arise.

More particularly, these serious conditions often require suctioning with the use of a very narrow tube or catheter, called a suction catheter, that extends through the nostril and into the sinus cavity or even beyond. A suction catheter can also be inserted through the mouth to do upper airway suctioning. Since suctioning must be done many times a day there is the potential for tissue damage to airway membranes and bleeding.

While insertion of the catheter is not particularly difficult for a nurse or other experienced person, often a parent observing such a procedure becomes apprehensive especially when the baby cries or gags while the catheter is being inserted and/or used. Understandably, a parent is often fearful and/or uncomfortable of attacking the task of inserting and using a suction catheter through the nose for fear that the child may be subjected to great discomfort or injury.

SUMMARY OF THE INVENTION

Because of the foregoing problems, the instant invention provides apparatus that enables oral and nasal suctioning to take place without inserting a catheter even when the baby is seriously or chronically ill. This is achieved by inserting a removable nozzle into the inlet of a flexible connecting tube whose output end is connected to a power driven suction pump. The apparatus is non-invasive in that nozzle is constructed to remain outside the nostril or be only slightly entered therein and be hand held while suctioning takes place. In this non-invasive way the apparatus accomplishes the same result as an invasive suction catheter In one embodiment of this invention the nozzle is the same as the stubby nozzle of a nose syringe which is used when suctioning requirements are infrequent and not much fluid must be removed from a relatively well infant. This nozzle is constructed of rigid material and is provided with a slightly convex conical surface that abuts the entrance to the baby's nostril while suctioning takes place. Another embodiment of this invention utilizes a nozzle that is conical and is tapered very gradually. In the latter embodiment the nozzle is constructed of relatively soft rubber-like material and is essentially the same shape as the elongated nozzle portion of an ear syringe.

In both embodiments of the instant invention, a flange having air passage holes may be included to partially block the oropharynx and nasopharynx openings when using the apparatus, and the nozzles are readily replaceable and are easy to unclog, sterilize and reuse, as contrasted with the suction catheter of the prior art which, because of its very narrow long passage, is at times easily clogged with copious secretions and should be discarded after use thereof.

OBJECTS OF THE INVENTION

Accordingly, the primary object of the instant invention is to provide suctioning apparatus for removing fluid secretions from seriously and chronically ill newborn babies, young infants, children and adults, which apparatus is convenient to operate, does not cause undue discomfort to the patient and does not present the potential to cause bleeding and/or tissue damage.

Another object is to provide apparatus of this type that is easy to clean, easy to sterilize, is reusable and is cost effective.

Still another object is to provide apparatus of this type that obviates the necessity for inserting a catheter through the nose or mouth of the patient but maintains an open airway and keeps the patient free from oral and nasal secretions.

BRIEF DESCRIPTION OF THE DRAWINGS

These objects as well as other objects of this invention shall become readily apparent after reading the following description of the accompanying drawings in which:

FIG. 1 is a side elevation of a prior art ear syringe.

FIG. 2 is a side elevation of a prior art nose syringe.

FIG. 3 is a perspective, in somewhat schematic form, of a prior art power driven suctioning apparatus for removing fluid secretions through the nose and/or mouth of a patient FIG. 4 is a side elevation of a suction nozzle connected to a suction connecting tube in accordance with the first embodiment of the instant invention.

FIG. 5 is a longitudinal cross-section of the nozzle taken through line 5—5 of FIG. 4 looking in the direction of arrows 5—5.

FIG. 6 is a view similar to FIG. 4 illustrating the second embodiment of the instant invention in which the nozzle is removably connected to one end of an adapter whose other end is inserted into a suction connecting tube.

FIGS. 7 and 9 are views illustrating an embodiment of the invention in which a flange is included in the apparatus.

FIG. 8 is a view of the apparatus shown in FIG. 7 along the direction of arrow A.

DETAILED DESCRIPTION OF THE PREFERRED EMBODIMENTS

Manually operated ear syringe 11 of FIG. 1 includes hollow bulbous portion 12 having narrow transverse extension 14 whose free end tapers gradually to form nozzle 15. Syringe 11 is a one piece unit constructed of flexible rubber-like material Air or other fluid within bulb 12 is ejected through the free end of nozzle 15 by manually squeezing bulb 12.

Prior art nose syringe 20 of FIG. 2 includes hollow pear shaped container 21 constructed of flexible rubber-like material, and removable nozzle 22 that extends from the narrow end of container 21. Nose syringe 20 is intended to provide suction at the free or intake end of nozzle 22, at its left end when viewed in FIG. 2. Suction is developed by manually squeezing container 21 to collapse same, and then releasing the collapsed container 21.

FIG. 3 illustrates a power operated device for suctioning fluid, and includes electrically operated suction pump unit 25 having master ON/OFF switch 26 and suction level selector control 27 both mounted on sidewall 28 of housing 29. Top 31 of housing 29 is fitted with suction level meter 32 and screen covered exhaust opening 33 which is downstream of suction input port 35 on end wall 34 of housing 29. The downstream end of flexible plastic tubing 36 is connected to suction pump 25 at input port 35 thereof. Fluid collecting container 37 having removable cap 38 is connected to tubing 36 by splitting the latter transversely and connecting same to respective hollow elbows 41, 42 that extend upward from cap 38. Hollow control device 43 extends upstream from the upstream end of tubing 36 and flexible plastic catheter 44 extends upstream from hollow control device 43. The latter includes longitudinal section 46 and transverse control section 47. The interiors of sections 46, 47 are in communication with each other and the passage through control section 47 is open at the end thereof remote from section 46 This latter passage is so much greater in cross-section than the cross-section of the very small diameter longitudinal passage through catheter 44 that the suction developed through operation of suction pump 25 does not normally provide suction at the free end of catheter 44. However, when the passage through control portion 47 is closed, by utilizing a finger, the suction generated by pump 25 extends to the free end of catheter 44.

In accordance with the instant invention control device 46 and catheter 44 are replaced by rigid nozzle 22 which, as seen in FIG. 4, is inserted directly into the upstream end of suction tubing 36. Conical surface 51 at the upstream end of nozzle 22 is, as best seen in FIG. 5, slightly convex. The apparatus of FIG. 4 is utilized by having an attendant (nurse, parent, etc.) hold nozzle 22 so that conical surface 51 engages the baby's nose covering a nostril thereof near its outer end so that intake opening 52 is aligned with the child's nostril and fluid secretions can be withdrawn from that nostril through opening 52 (FIG. 5), into nozzle 22 and then through the upstream portion of suction tubing 36 into container 37. The shape and size of conical surface 51 in relation to the nostril opening is such that very little if any of nozzle 22 extends into the nostril, yet nozzle 22 covers the open end of the nostril.

In the second embodiment of the instant invention (FIG. 6) gradually tapered conical nozzle 75 is removably connected by means of hollow rigid plastic adapter 61 to the upstream end of suction tubing 36. Nozzle 75 is constructed of a relatively soft flexible rubberlike material. In fact, nozzle 75 may be formed by cutting extension 14 (FIG. 1) at line 62 and utilizing that portion of extension 14 to the left of line 62. It is intended that nozzle 75 be sized and shaped so that it can be readily inserted but will not extend very far into the baby's or other patient's nostril, and the soft nature of the rubberlike material constituting nozzle 75 will not cause discomfort or injury.

In both embodiments of the invention a flange 100 (FIGS. 7-9) may be located on the suction tubing 36 adjacent nozzle 22 or 75. Flange 100 may be an integral piece of nozzle 22 or 75, or may be a removable element. Flange 100 blocks the oropharynx or nasopharynx opening when the apparatus of the invention is used to suction secretions. Apertures 110, 120, 130 and 140 are located in flange 100 to allow for limited flow of air therethrough to avoid a total vacuum within the oropharynx or nasopharynx. It will be understood that flange 100 may have any suitable shape, a round flange being depicted in FIG. 9, be any suitable material, such as plastic or silicone rubber, and include any suitable number of and shaped apertures.

Although the present invention has been described in connection with a plurality of preferred embodiments thereof, many other variations and modifications will now become apparent to those skilled in the art. It is preferred, therefore, that the present invention be limited not by the specific disclosure herein, but only by the appended claims.

What is claimed is:

1. Apparatus for maintaining a patient's upper airway clear by removing fluid secretions through such patient's oropharynx and nasopharynx, said apparatus including:
    power driven first means for generating suction at an input port thereof;
    flexible connecting tube means having a first end operatively connected to said input port, and a second end remote from said first end;
    removable nozzle means operatively connected to said second end; said nozzle means being operatively constructed to be operatively positioned and maintained manually at oropharynx and nasopharynx openings for suction removal of fluid secretions therethrough; said nozzle means being operatively constructed and proportioned relative to such openings to permit no more than minimal insertion of the nozzle means through such openings; and said nozzle means including a flange having at least one aperture therethrough, said flange being located adjacent said removable nozzle means for partially blocking air flow into and out of said oropharynx and nasopharynx openings during said suction removal.

2. Apparatus as set forth in claim 1, wherein said nozzle means includes a conical surface adapted to confront a body portion through which fluid is being removed.

3. Apparatus as set forth in claim 2, wherein said conical surface is slightly convex when viewed in cross-section.

4. Apparatus as set forth in claim 3, wherein said nozzle means is constructed of rigid material.

5. Apparatus as set forth in claim 3, wherein said nozzle means is also adapted to be used as a nozzle means of a manually operated nose syringe.

6. Apparatus as set forth in claim 1, wherein said conical surface tapers very gradually and the nozzle means is constructed of relatively soft rubber-like material.

7. Apparatus as set forth in claim 6, wherein said nozzle means is essentially the same shape as that of a nozzle portion of a manually operated ear syringe.

* * * * *